United States Patent [19]

Kikuchi et al.

[11] Patent Number: 5,330,835
[45] Date of Patent: Jul. 19, 1994

[54] SEAMLESS CAPSULE AND PROCESS FOR PRODUCING THE SAME

[75] Inventors: Yukio Kikuchi; Ryosei Kamaguchi, both of Osaka, Japan

[73] Assignee: Morishita Jintan Co., Ltd., Osaka, Japan

[21] Appl. No.: 922,752

[22] Filed: Jul. 31, 1992

[30] Foreign Application Priority Data

Jul. 31, 1991 [JP] Japan ................................. 3-191784

[51] Int. Cl.$^5$ .......................... A61K 9/50; A61K 9/66; B01J 13/04
[52] U.S. Cl. .................... 428/402.22; 264/4.4; 424/452; 424/455; 424/456; 424/492; 426/98; 426/103; 426/534; 428/402.2
[58] Field of Search ................. 264/4.1, 4.3, 4.32, 264/4.33, 4.4; 428/402.2, 402.22; 426/98, 103, 534; 424/452, 455, 456, 492

[56] References Cited

U.S. PATENT DOCUMENTS

| | | | |
|---|---|---|---|
| 2,780,355 | 2/1957 | Palmero et al. | 424/452 |
| 3,126,321 | 3/1964 | Kurtz | 424/456 X |
| 3,376,199 | 4/1968 | Coles et al. | 424/455 X |
| 3,558,323 | 1/1971 | Cannalonga et al. | 426/98 X |
| 3,623,997 | 11/1971 | Powell | 428/422.4 X |
| 3,962,383 | 6/1976 | Hagiwara et al. | 264/4 |
| 4,217,241 | 8/1980 | Okada et al. | 264/4.32 |
| 4,695,466 | 9/1987 | Morishita et al. | 424/456 |
| 4,708,834 | 11/1987 | Cohen et al. | 264/4.3 |
| 4,832,967 | 5/1989 | Autant et al. | 426/98 X |
| 5,037,698 | 8/1991 | Brunel | 428/402.2 |
| 5,082,661 | 1/1992 | Melnick et al. | 424/456 X |

FOREIGN PATENT DOCUMENTS

| | | | |
|---|---|---|---|
| 2201129 | 4/1974 | France . | |
| 0192061 | 10/1984 | Japan | 426/98 |
| 471597 | 4/1969 | Switzerland . | |

OTHER PUBLICATIONS

Database WPIL, accession No. 87-359742 (51), Derwent Publications Ltd., London, GB; & JP-A-62263128 (Freund Sangyko K.K) Nov. 16, 1987.
Database WPI, accession No. 76-17781X (10), Derwent Publications Ltd., London, GB: & JP-A-51008177 (Morishita Jintan K.K.) Jan. 22, 1976.

*Primary Examiner*—Richard D. Lovering
*Attorney, Agent, or Firm*—Wegner, Cantor, Mueller & Player

[57] ABSTRACT

A seamless capsule comprising a content and a film for coating said content is disclosed. The content is a hydrophilic substance. A viscous liquid having a viscosity of not more than 1000 cp at 100° C. which is scarcely miscible with water is present between the content and the film. There is also disclosed a process for producing a seamless capsule which comprises simultaneously extruding a film solution for the seamless capsule, a hydrophilic substance solution and a viscous liquid which is scarcely miscible with water into a cooling solution from a concentrically arranged multiple nozzle composed of at least three nozzles, an outermost nozzle, an innermost nozzle and at least one intermediate nozzle placed in the middle position between the above nozzles, respectively, the diameter of said nozzle gradually increasing in that order.

9 Claims, 1 Drawing Sheet

SEAMLESS CAPSULE AND PROCESS FOR PRODUCING THE SAME

FIELD OF THE INVENTION

The present invention relates to a seamless capsule containing a hydrophilic substance as a content, and a process for producing the same.

BACKGROUND OF THE INVENTION

Regarding seamless capsules which have hitherto been used for various applications, substances which can be encapsulated are specifically limited to lipophilic substances such as liquid oil, powder-suspended oil and the like.

Hydrophilic substances are not actually encapsulated in a stable state, because hydrophilic substances generally employ water as a solvent which makes the capsules soften on and after encapsulation.

In Japanese Patent Kokai No. 03-52639, there is disclosed a method for encapsulating a hydrophilic substance wherein a lower fatty acid ester of sucrose is provided between the hydrophilic substance and a film. Although the method actually produces a seamless capsule containing a hydrophilic substance, there is a problem in that the water content of the hydrophilic substance increasingly transfers to the film in the form of water vapor to soften the capsule or adhere to it, particularly at high temperatures (not less than 30° C.). Further, propagation of mold or bacterium is liable to arise with time due to the water content transferred to the film. There is also a quality problem in design.

OBJECTS OF THE INVENTION

One object of the present invention is to provide an excellent method for encapsulating a hydrophilic substance.

Another object of the present invention is to provide a seamless capsule having excellent stability in quality and high commercial value.

These objects as well as other objects and advantages of the present invention will become apparent to those skilled in the art from the following description with reference to the accompanying drawings.

SUMMARY OF THE INVENTION

Figure 1:
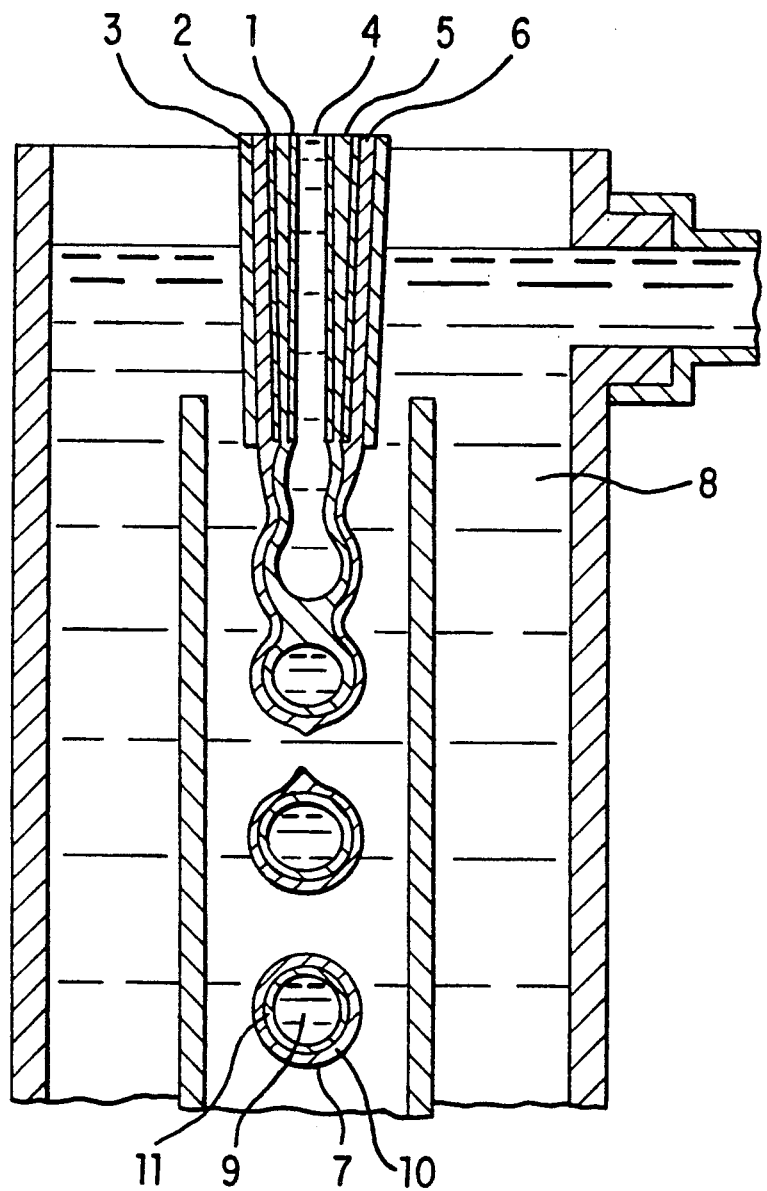
FIG. 1 is a schematic cross section illustrating one embodiment of the nozzle part of an apparatus which is suitable for producing the seamless capsule of the present invention.

The present invention provides a seamless capsule which comprises a content and a film for coating said content, said content being a hydrophilic substance dissolved in a solvent having strong hygroscopicity, and a viscous liquid having a viscosity of not more than 1000 cp at 100° C. which is scarcely miscible with water being present between said content and said film.

Further, the present invention also provides a process for producing a seamless capsule which comprises simultaneously extruding a film solution for the seamless capsule, a hydrophilic substance solution and a viscous liquid which is scarcely miscible with water into a cooling solution from a concentrically arranged multiple nozzle composed of at least three nozzles, an outermost nozzle, an innermost nozzle and at least one intermediate nozzle placed in the middle position between the above nozzles, respectively, the diameter of said nozzle gradually increasing in that order.

DETAILED DESCRIPTION OF THE INVENTION

In the present invention, the content which can be seamless-encapsulated is not limited to a specific one and can be anyone which can dissolve in a solvent having strong hygroscopicity and become a liquid under heating to be ejected from a nozzle. Examples thereof include various pharmaceutical solutions, foods, cosmetics, flavors, industrial chemicals and the like.

The solvent having strong hygroscopicity is not specifically limited and examples thereof include alcohols such as polyethylene glycol, propylene glycol, glycerin, ethanol, methanol and the like.

The film substance of the seamless capsule used in the present invention is not specifically limited and suitable examples thereof include a film-forming substance obtained by treating a composition containing gelatin, agar and low methoxyl pectin or sodium alginate with a compound by which an aqueous solution of low methoxyl pectin or sodium alginate can be gelated; a film-forming substance obtained by subjecting a water-soluble polyvalent alcohol or water-soluble derivative thereof to a gelation treatment; a film-forming substance obtained by treating a mixture of a composition containing gelatin and agar and a composition containing gelatin and low methoxyl pectin or sodium alginate with a compound by which an aqueous solution of low methoxyl pectin and sodium alginate can be gelated and the like. Gelatin, agar and water-soluble polyvalent alcohol or water-soluble derivative thereof having the same grade as that of which is used for producing a conventional capsule may be employed as it is.

The water-soluble polyvalent alcohol or water-soluble derivative thereof is not specifically limited and examples thereof include glycerin, polyglycerin, sorbitol, ethylene glycol, polyethylene glycol, propylene glycol, polypropylene glycol, ethylene oxide-propylene oxide copolymer, oligosaccharide, sugar ester, glyceride, sorbitan ester and the like.

The amount of gelatin to be used is normally 60 to 90% by weight based on the total weight of the capsule film. The amount of agar is 60 to 90% by weight based on the total weight of the capsule film. Suitable low methoxyl pectin is that having a molecular weight of not less than 200,000 and a methoxylation degree of 1 to 6% (preferably 3.5 to 5%) and the amount thereof is 5 to 20% by weight, preferably 10 to 15% by weight based on the total weight of the film. The amount of the water-soluble polyvalent alcohol or water-soluble derivative thereof is 10 to 30% by weight, preferably 15 to 25% by weight based on the total weight of the film. The amount of gelatin is 65 to 75% by weight (in the case of using with agar), 65 to 75% by weight (in the case of using with low methoxyl pectin) and 65 to 85% by weight (in the case of using with sodium alginate), respectively, based on the total weight of the mixture. In the case of use with sodium alginate, the amount of gelatin is 1 to 10% by weight, preferably 3 to 5% by weight based on the total weight of the film. As the compound by which an aqueous solution of low methoxyl pectin or sodium alginate can be gelated, for example, there are salts of polyvalent metal having at least two valences. In the case of low methoxyl pectin, water-soluble salts of calcium, magnesium and the like may be suitably used. In the case of sodium alginate, water-soluble calcium salts such as calcium chloride, calcium phosphate and the like may be used.

In the seamless capsule of the present invention, a viscous liquid which is scarcely miscible with water is present between the above film and content.

The viscous liquid which is scarcely miscible with water may be anyone having a viscosity of not more than 1000 cp at 100° C. Examples thereof include emulsifiers, oils, resins and the like and they may be used alone or in combination thereof. Examples of the emulsifier include nonionic emulsifiers having HLB value of 2 to 8 such as sucrose fatty acid ester, propylene glycol fatty acid ester, glycerin fatty acid ester (e.g. long chain fatty acid triglyceride, medium chain fatty acid triglyceride, etc.), ampho-ionic emulsifiers such as lecithin or a mixture thereof. Examples of oils include vegetable fats and oils, animal fats and oils and mineral oil of which solubility in 100 g of absolute alcohol at 150° C. is not more than 50 g, for example, sesame oil, coffee oil, rapeseed oil, brown rice oil, liquid paraffin or mixture thereof are preferred. Further, dl-α-tocopherol, isobutylene polymers (e.g. polybutylene, polybutene, etc.), resins (e.g. silicone resin, vinyl acetate resin, etc.) and the like can be used. Further, as described above, the viscous liquid is present between the content and film in the case of producing the capsule. However, it is not necessarily required that the viscous liquid is present between the content and film, and it may be present in the content in the separate state.

Hereinafter, a process for producing the seamless capsule of the present invention will be explained with reference to the accompanying drawing.

FIG. 1 is a schematic cross section illustrating one embodiment of the nozzle part of an apparatus which is suitable for producing the seamless capsule of the present invention.

A capsule content 4 which is supplied into a nozzle part is extruded from an inner nozzle (first nozzle) 1 and a viscous liquid which is scarcely miscible with water is extruded from an annular pore tip of an intermediate nozzle (second nozzle) 2 and, at the same time, a film solution for a seamless capsule 6 is extruded from an annular pore tip part of an outer nozzle (third nozzle) 3, and then a three-phase composite jet thus obtained is ejected into a cooling solution 8 to obtain a seamless capsule 7 of the present invention. The capsule 7 comprises a central core 9, a film-forming outer wall 10 and a discrete layer 11 between the central core 9 and the outer wall 10.

In this case, when the content jet 3 is a two-phase jet, a triplex soft capsule is obtained and, when it is a three-phase jet, a quadruplex soft capsule is obtained. Similarly, a desired multiplex soft capsule 7 is produced. Further, the other nozzle, for example, a medium nozzle itself may be multiplex.

The filler is liquid and, therefore, by providing a suitable vibration to the composite jet flow using a vibration means, dropping of the jet flow may be improved. whereby, encapsulation is easily conducted, which results in uniform particle size.

The seamless capsule thus produced as described above may be dried as it is and then washed.

In general, as the film of the seamless capsule, water-soluble film substances such as gelatin may be used as the film. Particularly, in the production of the seamless capsule by a dropping method, an aqueous solution of the film substance is extruded out from a nozzle and, therefore, the water content of the film substance is large (not less than 70%). Accordingly, when a hydrophilic substance containing alcohols as a solvent is used as the content, the film solution is reacted with alcohol and, therefore, no capsule can be formed. However, according to the present invention, the reaction of the film solution with alcohol can be prevented by providing a viscous liquid which is scarcely miscible with water between the film and the content (hydrophilic substance), and a seamless capsule of a hydrophilic substance containing alcohol as a solvent can be easily obtained by a dropping method. Further, by using alcohol as a solvent of the content, softening of the film and propagation of mold or bacterium due to the water content transferred to the film can be prevented and stable quality can be obtained.

EXAMPLES

The following Examples further illustrate the present invention in detail but are not to be construed to limit the scope thereof.

A seamless capsule in the following Examples is composed of a content solution (solution I), a viscous liquid (solution II) which is present between a film solution and the content solution and the film solution (solution III).

EXAMPLE 1

By using polyethylene glycol 400 (molecular weight: 380 to 420) as a solvent for a solution I and using sucrose fatty acid ester (SAIB) as a viscous liquid (solution II), a mouth refrigerant capsule of 3.2 mmφ containing herb extract was produced.

| Ingredients | (Formulation 1) Amount (% by weight) | Ratio (%) |
|---|---|---|
| Solution I: | | |
| Polyethylene glycol | 96.5 | |
| Herb extract | 2.0 | 70 |
| Sweetener | 1.0 | |
| Flavor | 0.5 | |
| Solution II: | | |
| SAIB | 80.0 | |
| l-Menthol | 15.0 | 20 |
| Flavor | 5.0 | |
| Solution III: | | |
| Gelatin | 20.0 | |
| D-sorbitol | 5.0 | 10 |
| Water | 75.0 | |

By using a concentric triplex nozzle, a herb extract solution containing PEG 400 as a solvent (solution I) was extruded from an inner nozzle and a l-menthol solution containing SAIB as a main ingredient (solution II) heated to 80° C. was extruded from an intermediate nozzle and, at the same time, a gelatin solution (solution III) heated to 60° C. was extruded from an outer nozzle to form a three-phase jet in a ratio as shown in Formulation 1, and then the jet was injected into a vegetable oil cooled to 12° C., which was descending at a flow rate of 0.3 m/second, to obtain a seamless capsule. Regarding the capsule after drying, no softening and dissolution were observed at high temperature (not less than 30° C.), and it was stable. The capsule was transparent and had good mouth feel and taste.

EXAMPLE 2

By using PEG 400 (molecular weight: 380 to 420) as a solvent for a solution I and using sucrose fatty acid ester (SAIB) as a viscous liquid (solution II), a mouth refrigerant capsule of 3.2 mmφ containing herb medicine extract was produced.

| Ingredients | (Formulation 2) Amount (% by weight) | Ratio (%) |
| --- | --- | --- |
| Solution I: | | |
| Polyethylene glycol | 97.0 | |
| Gambir extract | 1.5 | 65 |
| Sweetener | 1.0 | |
| Flavor | 0.5 | |
| Solution II: | | |
| SAIB | 80.0 | |
| l-Menthol | 15.0 | |
| Cinnamon oil | 1.0 | 20 |
| Fennel oil | 1.6 | |
| Clove oil | 1.6 | |
| Flavor | 0.3 | |
| Solution III: | | |
| Gelatin | 20.0 | |
| D-sorbitol | 5.0 | 15 |
| Water | 75.0 | |

According to the same preparation condition as that described in Example 1, a seamless capsule was obtained. Regarding the capsule after drying, no softening and dissolution were observed at high temperature (not less than 30° C.), and it was stable. The herb medicine capsule was transparent and had good mouth feel and taste.

EXAMPLE 3

By using ethyl alcohol as a solvent for a solution I and using coffee oil as a viscous liquid (solution II), a coffee capsule of 3.2 mmφ containing coffee extract was produced.

| Ingredients | (Formulation 3) Amount (% by weight) | Ratio (%) |
| --- | --- | --- |
| Solution I: | | |
| Ethyl alcohol | 60.0 | |
| Polyvinyl pyrrolidone (PVP) | 25.0 | 65 |
| Sweetener | 1.0 | |
| Coffee flavor | 14.0 | |
| Solution II: | | |
| Coffee oil (press oil) | 100.0 | 20 |
| Solution III: | | |
| Gelatin | 12.0 | |

| Ingredients | (Formulation 3) Amount (% by weight) | Ratio (%) |
| --- | --- | --- |
| Lactose | 8.0 | 15 |
| Water | 75.0 | |

According to the same preparation condition as that described in Example 1, a seamless capsule was obtained. Regarding the capsule after drying, no softening and dissolution were observed at high temperature (not less than 30° C.), and it was stable. The coffee capsule was transparent and had good mouth feel and taste.

What is claimed is:

1. A seamless capsule, comprising:
   a central core layer comprising a hydrophilic substance dissolved in an alcohol;
   a film forming an outer wall layer for the capsule; and
   a discrete layer of a viscous liquid having a viscosity of not more than 1000 cp at 100° C., said viscous liquid being scarcely miscible with water, wherein said discrete layer of viscous liquid is between said central core and said film.

2. The seamless capsule according to claim 1, wherein said viscous liquid is a nonionic emulsifier having HLB value of 2 to 8, an ampho-ionic emulsifier or a mixture of these emulsifiers.

3. The seamless capsule according to claim 1, wherein said viscous liquid is selected from the group consisting of vegetable fats and oils, animal fats and oils and mineral oil having a solubility in 100 g of absolute alcohol at 15° C. which is not more than 50 g.

4. The seamless capsule according to claim 1, wherein said viscous liquid is dl-α-tocopherol.

5. The seamless capsule according to claim 1, wherein said viscous liquid is isobutylene polymer.

6. The seamless capsule according to claim 1, wherein said viscous liquid is silicone resin or vinyl acetate resin.

7. The seamless capsule according to claim 1, wherein said film comprises gelatin.

8. A process for producing a seamless capsule, comprising:
   supplying a hydrophilic substance solution to an innermost orifice of a concentrically arranged multiple nozzle comprising at least three orifices;
   supplying a film solution for the seamless capsule to an outermost orifice of the multiple nozzle;
   supplying a viscous liquid which is scarcely miscible with water to an intermediate orifice of the multiple nozzle; and
   simultaneously extruding the film solution, the viscous liquid and the hydrophilic substance solution into a cooling solution.

9. The process of claim 8, wherein the cooling solution is a vegetable oil.

* * * * *